(12) United States Patent
Lockemeyer et al.

(10) Patent No.: US 7,485,597 B2
(45) Date of Patent: *Feb. 3, 2009

(54) METHOD FOR IMPROVING THE SELECTIVITY OF A CATALYST AND A PROCESS FOR THE EPOXIDATION OF AN OLEFIN

(75) Inventors: John Robert Lockemeyer, Sugar Land, TX (US); Randall Clayton Yeates, Sugar Land, TX (US); Donald Reinalda, Amstersam (NL)

(73) Assignee: Shell Oil Company, Houston, TX (US)

( * ) Notice: Subject to any disclaimer, the term of this patent is extended or adjusted under 35 U.S.C. 154(b) by 586 days.

This patent is subject to a terminal disclaimer.

(21) Appl. No.: 10/606,440

(22) Filed: Jun. 26, 2003

(65) Prior Publication Data
US 2004/0049061 A1    Mar. 11, 2004

Related U.S. Application Data

(60) Provisional application No. 60/392,657, filed on Jun. 28, 2002.

(51) Int. Cl.
| | |
|---|---|
| B01J 21/02 | (2006.01) |
| B01J 27/00 | (2006.01) |
| B01J 27/198 | (2006.01) |
| B01J 27/188 | (2006.01) |
| B01J 27/19 | (2006.01) |
| B01J 27/192 | (2006.01) |
| B01J 27/185 | (2006.01) |
| B01J 27/182 | (2006.01) |
| B01J 27/057 | (2006.01) |
| B01J 27/02 | (2006.01) |
| B01J 27/047 | (2006.01) |
| B01J 23/00 | (2006.01) |
| B01J 23/48 | (2006.01) |
| B01J 23/50 | (2006.01) |

(52) U.S. Cl. .................. 502/216; 502/202; 502/208; 502/209; 502/210; 502/211; 502/212; 502/213; 502/214; 502/215; 502/219; 502/305; 502/306; 502/307; 502/308; 502/309; 502/310; 502/311; 502/312; 502/313; 502/314; 502/315; 502/316; 502/317; 502/318; 502/319; 502/320; 502/321; 502/322; 502/323; 502/324; 502/344; 502/347; 502/348

(58) Field of Classification Search .......... 502/344, 502/347, 348, 202, 305–324, 219, 208–216
See application file for complete search history.

(56) References Cited

U.S. PATENT DOCUMENTS

| | | | |
|---|---|---|---|
| 2,219,575 A | 10/1940 | McNamee et al. ......... 260/348 |
| 3,962,136 A * | 6/1976 | Nielsen et al. ............. 502/243 |
| 4,007,135 A * | 2/1977 | Hayden et al. ............. 502/317 |
| 4,097,414 A | 6/1978 | Cavitt ....................... 252/476 |
| 4,102,820 A | 7/1978 | Cavitt ....................... 252/463 |
| 4,206,128 A | 6/1980 | Cavitt ................... 260/348.34 |
| 4,224,194 A | 9/1980 | Cavitt ....................... 252/476 |
| 4,321,206 A | 3/1982 | Cavitt ................... 260/348.34 |
| 4,389,338 A | 6/1983 | Mitsuhata et al. .......... 252/463 |
| 4,400,559 A | 8/1983 | Bhise ........................ 568/858 |
| 4,410,453 A | 10/1983 | Kiovsky et al. ............ 502/253 |
| 4,428,863 A | 1/1984 | Fry ............................... 502/8 |
| 4,465,754 A | 8/1984 | Kuin et al. ................. 430/109 |
| 4,508,927 A | 4/1985 | Bhise et al. ................ 568/858 |
| 4,555,501 A | 11/1985 | Armstrong ................. 502/243 |
| 4,761,394 A | 8/1988 | Lauritzen .................. 502/348 |
| 4,766,105 A * | 8/1988 | Lauritzen .................. 502/216 |
| 4,822,900 A | 4/1989 | Hayden ..................... 549/534 |
| 4,845,296 A | 7/1989 | Ahmed et al. .............. 564/477 |
| 4,874,879 A | 10/1989 | Lauritzen et al. .......... 549/536 |
| 4,939,114 A | 7/1990 | Nojiri et al. ............... 502/348 |

(Continued)

FOREIGN PATENT DOCUMENTS

EP    003642 A2    8/1979

(Continued)

OTHER PUBLICATIONS

Kirk-Othmer's Encyclopedia Of Chem. Tech., 3rd Ed., vol. 9 (1980). pp. 445-447, no month.

(Continued)

Primary Examiner—Patricia L Hailey

(57) ABSTRACT

A method for improving the selectivity of a supported highly selective epoxidation catalyst comprising silver in a quantity of at most 0.17 g per $m^2$ surface area of the support, which method comprises contacting the catalyst, or a precursor of the catalyst comprising the silver in cationic form, with a feed comprising oxygen at a catalyst temperature above 250° C. for a duration of up to 150 hours, and subsequently decreasing the catalyst temperature to a value of at most 250° C.; and a process for the epoxidation of an olefin, which process comprises contacting a supported highly selective epoxidation catalyst comprising silver in a quantity of at most 0.17 g per $m^2$ surface area of the support, or a precursor of the catalyst comprising the silver in cationic form, with a feed comprising oxygen at a catalyst temperature above 250° C. for a duration of up to 150 hours, and subsequently decreasing the catalyst temperature to a value of at most 250° C. and contacting the catalyst with the feed comprising the olefin and oxygen.

24 Claims, No Drawings

U.S. PATENT DOCUMENTS

| | | | | |
|---|---|---|---|---|
| 4,994,588 | A | 2/1991 | Kapicak et al. | 549/534 |
| 5,051,395 | A * | 9/1991 | Mitchell et al. | 502/348 |
| 5,100,859 | A | 3/1992 | Gerdes et al. | 502/439 |
| 5,102,848 | A | 4/1992 | Soo et al. | 502/218 |
| 5,155,242 | A | 10/1992 | Shankar et al. | 549/534 |
| 5,187,140 | A * | 2/1993 | Thorsteinson et al. | 502/348 |
| 5,380,697 | A | 1/1995 | Matusz et al. | 502/348 |
| 5,395,812 | A | 3/1995 | Nagase et al. | 502/238 |
| 5,407,888 | A * | 4/1995 | Herzog et al. | 502/317 |
| 5,418,202 | A | 5/1995 | Evans et al. | 502/348 |
| 5,444,034 | A | 8/1995 | Rizkalla | 502/347 |
| 5,504,052 | A | 4/1996 | Rizkalla et al. | 502/347 |
| 5,504,053 | A * | 4/1996 | Chou et al. | 502/348 |
| 5,646,087 | A | 7/1997 | Rizkalla et al. | 502/347 |
| 5,736,483 | A * | 4/1998 | Rizkalla | 502/347 |
| 5,739,075 | A | 4/1998 | Matusz | 502/302 |
| 5,770,746 | A | 6/1998 | Cocker et al. | 549/534 |
| 5,780,656 | A * | 7/1998 | Rizkalla et al. | 549/534 |
| 5,801,259 | A | 9/1998 | Kowaleski | 549/536 |
| 5,854,167 | A * | 12/1998 | Rizkalla et al. | 502/216 |
| 5,856,534 | A | 1/1999 | Cooker et al. | 549/534 |
| 5,929,259 | A | 7/1999 | Lockemeyer | 549/534 |
| 6,087,299 | A | 7/2000 | Grub et al. | 502/347 |
| 6,368,998 | B1 | 4/2002 | Lockemeyer | 502/347 |
| 6,372,925 | B1 | 4/2002 | Evans et al. | 549/536 |
| 6,498,122 | B2 | 12/2002 | Nakashiro | 502/347 |
| 6,511,938 | B1 * | 1/2003 | Liu et al. | 502/347 |
| 6,579,825 | B2 * | 6/2003 | Lockemeyer | 502/347 |
| 6,600,056 | B1 | 7/2003 | Mikawa et al. | 549/534 |
| 6,656,874 | B2 * | 12/2003 | Lockemeyer | 502/347 |
| 6,750,173 | B2 * | 6/2004 | Rizkalla et al. | 502/348 |
| 6,762,311 | B2 * | 7/2004 | Rizkalla et al. | 549/534 |
| 6,908,879 | B1 | 6/2005 | Shima et al. | 502/242 |
| 7,102,022 | B2 | 9/2006 | Evans et al. | 549/536 |
| 2002/0010094 | A1 | 1/2002 | Lockemeyer | 502/439 |
| 2003/0162984 | A1 | 8/2003 | Lockemeyer et al. | 549/534 |
| 2003/0191019 | A1 | 10/2003 | Rizkalla et al. | 502/243 |
| 2004/0049061 | A1 | 3/2004 | Lockemeyer et al. | 549/536 |
| 2004/0110971 | A1 | 6/2004 | Evans et al. | 549/534 |
| 2007/0185339 | A1 | 8/2007 | Lu | 549/534 |

FOREIGN PATENT DOCUMENTS

| | | |
|---|---|---|
| EP | 0026605 | 4/1984 |
| EP | 211521 | 2/1987 |
| EP | 266.015 A1 | 5/1988 |
| EP | 0161930 | 5/1989 |
| EP | 326.392 A1 | 8/1989 |
| EP | 352.849 A1 | 1/1990 |
| EP | 352.850 | 1/1990 |
| EP | 0226234 | 8/1990 |
| EP | 0448157 | 9/1991 |
| EP | 567.273 | 10/1993 |
| EP | 0496470 | 9/1994 |
| EP | 716.884 A2 | 6/1996 |
| EP | 0808215 | 9/1998 |
| EP | 999.130 A2 | 8/1999 |
| EP | 0806984 | 3/2000 |
| EP | 1 002 575 A2 | 5/2000 |
| GB | 1.170.663 | 11/1969 |
| GB | 1.191.983 A | 5/1970 |
| GB | 1.489.335 | 10/1977 |
| SU | 1255200 | 3/1982 |
| WO | 95/05896 | 3/1995 |
| WO | WO9517957 | 7/1995 |
| WO | 9604989 A1 | 2/1998 |
| WO | WO9845280 | 10/1998 |
| WO | 00/15332 | 3/2000 |
| WO | 00/15333 | 3/2000 |
| WO | 00/15334 | 3/2000 |
| WO | 00/15335 | 3/2000 |
| WO | WO 01/96324 | 12/2001 |
| WO | 2004/002972 A2 | 1/2004 |
| WO | WO2004002954 | 1/2004 |
| WO | WO2004092148 | 10/2004 |
| WO | WO2004101141 | 11/2004 |
| WO | WO2005097318 | 10/2005 |
| WO | WO2006020718 | 2/2006 |

OTHER PUBLICATIONS

Letter to the European Patent Office. dated Jul. 11, 2000. relating to Euopean Patent Application No. 95203469.2-2104. publication No. 716884.

Brunauer. Emmet and Teller. J. of American Chem. Society. vol. 60 (1938): pp. 309-316, no month.

Beilstein Institute for Organic Chemistry. Frankfurt-Main. DE. XP002296657 . J. Am. Chem. Society. vol. 56. (1934): pp. 1870-1872, no month.

International Search Report. PCT/US2004/010457.

International Search Report, dated Oct. 30, 2003, for PCT/US2003/19828.

International Preliminary Examination Report, dated Oct. 10, 2004, for PCT/US2003/19828.

Written Opinion, dated May 6, 2004, for PCT/US2003/19828.

International Search Report, dated Feb. 20, 2004, for PCT/US2003/20095.

International Preliminary Examination Report, dated Oct. 5, 2004, for PCT/US2003/20095.

Written Opinion, dated Mar. 16, 2004, for PCT/US2003/20095.

International Search Report, dated Jun. 11, 2004, for PCT/US2003/19827.

International Preliminary Examination Report, dated Oct. 27, 2004, for PCT/US2003/19827.

Written Opinion, dated Jul. 16, 2004, for PCT/US2003/19827.

Notice of Allowance for U.S. Appl. No. 11/670,325 dated May 30, 2008.

Office Communication for U.S. Appl. No. 11/670,325 dated May 30, 2008.

Perry, Robert H. et al, Perry's Chemical Engineers Handbook, 6th Ed., pp. 20-14 to 20-51 (1984).

International Patentability Report for PCT/US2004/010457 dated Aug. 18, 2005.

Office Action for U.S. Appl. No. 10/816,480 dated Jun. 23, 2005.

* cited by examiner

METHOD FOR IMPROVING THE SELECTIVITY OF A CATALYST AND A PROCESS FOR THE EPOXIDATION OF AN OLEFIN

This application claims the benefit of U.S. Provisional Application No. 60/392,657 filed Jun. 28, 2002 the entire disclosure of which is hereby incorporated by reference.

FIELD OF THE INVENTION

The invention relates to a method for improving the selectivity of a highly selective epoxidation catalyst. The invention also relates to a process for the epoxidation of an olefin, which process includes the said method of this invention.

BACKGROUND OF THE INVENTION

The catalytic epoxidation of olefins over supported silver catalysts, yielding the corresponding olefin oxide, has been known for a long time. Conventional silver-based catalysts have provided the olefin oxides with notoriously low selectivity. For example, when using conventional catalysts in the epoxidation of ethylene, the selectivity towards ethylene oxide, expressed as a fraction of the ethylene converted, does not reach values above the 6/7 or 85.7 mole-% limit. Therefore, this limit has long been considered to be the theoretically maximal selectivity of this reaction, based on the stoichiometry of the reaction equation $$7C_2H_4 + 6O_2 \rightarrow 6C_2H_4O + 2CO_2 + 2H_2O,$$

cf. Kirk-Othmer's *Encyclopedia of Chemical Technology*, 3$^{rd}$ ed., Vol. 9, 1980, p. 445.

The selectivity determines to a large extent the economical attractiveness of an epoxidation process. For example, one percent improvement in the selectivity of the epoxidation process can reduce the yearly operating costs of a large scale ethylene oxide plant substantially.

The olefin oxide produced by the epoxidation process may be reacted with water, an alcohol or an amine to form a 1,2-diol, a 1,2-diol ether or an alkanolamine. Thus, 1,2-diols, 1,2-diol ethers and alkanolamines may be produced in a multi-step process comprising olefin epoxidation and converting the formed olefin oxide with water, an alcohol or an amine. Any improvement in the selectivity of the epoxidation process can also reduce the yearly operating costs in the overall process for the production of a 1,2-diol, a 1,2-diol ether or an alkanolamine.

Modern silver-based epoxidation catalysts are highly selective towards olefin oxide production. When using the modern catalysts in the epoxidation of ethylene the selectivity towards ethylene oxide can reach values above the 6/7 or 85.7 mole-% limit referred to. Such highly selective catalysts comprise, in addition to silver, a selectivity enhancing dopant which may be selected from rhenium, molybdenum, tungsten and nitrate- or nitrite-forming compounds, cf. for example U.S. Pat. No. 4,761,394 and U.S. Pat. No. 4,766,105.

SUMMARY OF THE INVENTION

The present invention provides a method for improving the selectivity of a supported highly selective epoxidation catalyst comprising silver in a quantity of at most 0.17 g per m$^2$ surface area of the support, which method comprises contacting the catalyst, or a precursor of the catalyst comprising the silver in cationic form, with a feed comprising oxygen at a catalyst temperature above 250° C. for a duration of up to 150 hours, and subsequently decreasing the catalyst temperature to a value of at most 250° C.

The invention also provides a process for the epoxidation of an olefin, which process comprises contacting a supported highly selective epoxidation catalyst comprising silver in a quantity of at most 0.17 g per m$^2$ surface area of the support, or a precursor of the catalyst comprising the silver in cationic form, with a feed comprising oxygen at a catalyst temperature above 250° C. for a duration of up to 150 hours, and subsequently decreasing the catalyst temperature to a value of at most 250° C. and contacting the catalyst with the feed comprising the olefin and oxygen.

The invention also provides a process for producing a 1,2-diol, 1,2-diol ether, or an alkanolamine, comprising converting an olefin oxide into the 1,2-diol, the 1,2-diol ether, or the alkanolamine, wherein the olefin oxide has been obtained by a process for the epoxidation of an olefin according to this invention.

DETAILED DESCRIPTION OF THE INVENTION

In accordance with this invention, the selectivity of a highly selective epoxidation catalyst can be improved by heat-treating the catalyst in the presence of oxygen at a temperature which is typically above the catalyst's normal initial operation temperature. This is unexpected in the light of the prior art. For example, U.S. Pat. No. 5,646,087 teaches to avoid the presence of oxygen when a silver-based catalyst is exposed to a high temperature, and a belief is expressed that at temperatures of 250° C. and higher oxygen is absorbed in substantial quantities into the bulk of the silver where it has an adverse effect on the catalyst characteristics.

It would seem that the heat treatment leads to a somewhat lower activity of the catalyst, which would result in a somewhat higher operating temperature during the catalyst's normal use. The higher operating temperature frequently leads to a reduction in the catalyst's lifetime, due to more rapid contact sintering. Therefore, without wishing to be bound by theory, it is preferred to avoid applying the present heat treatment to catalysts which have a high silver density on the support surface, i.e. the quantity of silver relative to the surface area of the support, in order to diminish contact sintering during the use of the catalysts.

The heat treatment may be applied to a catalyst before its first use in an epoxidation process, in which case, after the heat treatment, the temperature of the catalyst may be decreased to a level which is convenient, for example, for storage of the catalyst prior to its use in an epoxidation process. Alternatively, the heat treatment may be applied to a catalyst which is already in use in an epoxidation process, in which case the temperature of the catalyst may subsequently be decreased to a level suitable for operating the epoxidation process.

As used herein, a highly selective silver-based epoxidation catalyst is generally a catalyst which, when operated fresh, can exhibit in the gas phase epoxidation of ethylene a theoretical selectivity at zero oxygen conversion, $S_0$, of at least 6/7 or 85.7%. More in particular, this theoretical selectivity can be accomplished at a reaction temperature of 260° C. The value of $S_0$ for a given catalyst is found by operating the catalyst, in particular at a temperature of 260° C., in a range of gas hourly space velocities, resulting in a range of selectivity values and oxygen conversion values corresponding to the range of gas hourly space velocities employed. The selectivity values found are then extrapolated back to the theoretical selectivity at zero oxygen conversion, $S_O$. As used herein, the selectivity is the fraction of the olefin converted yielding the olefin oxide.

Generally, the highly selective silver-based epoxidation catalyst is a supported catalyst. The support may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is α-alumina.

The support is preferably porous and has preferably a surface area of at most 20 $m^2/g$, in particular from 0.1 to 20 $m^2/g$, more in particular from 0.5 to 10 $m^2/g$, and most in particular from 1 to 5 $m^2/g$. As used herein, the B.E.T. surface area is deemed to have been measured by the method as described in Brunauer, Emmet and Teller in *J. Am. Chem. Soc.* 60 (1938) 309-316.

A preferred alumina support, providing highly selective silver-based catalysts with an improved performance in terms of selectivity, activity and lifetime, has a surface area of at least 1 $m^2/g$, and a pore size distribution such that pores with diameters in the range of from 0.2 to 10 μm represent at least 70% of the total pore volume and such pores together provide a pore volume of at least 0.25 ml/g, relative to the weight of the support. Preferably, the pore size distribution is such that pores with diameters less than 0.2 μm represent from 0.1 to 10% of the total pore volume, in particular from 0.5 to 7% of the total pore volume; the pores with diameters in the range of from 0.2 to 10 μm represent from 80 to 99.9% of the total pore volume, in particular from 85 to 99% of the total pore volume; and the pores with diameters greater than 10 μm represent from 0.1 to 20% of the total pore volume, in particular from 0.5 to 10% of the total pore volume. Preferably, the pores with diameters in the range of from 0.2 to 10 μm provide a pore volume in the range of from 0.3 to 0.8 ml/g, in particular from 0.35 to 0.7 ml/g. Preferably, the total pore volume is in the range of from 0.3 to 0.8 ml/g, in particular from 0.35 to 0.7 ml/g. The surface area of the preferred support is typically at most 3 $m^2/g$. Preferably, the surface area is in the range of from 1.4 to 2.6 $m^2/g$.

A higher total pore volume is advantageous in view of a more efficient deposition of silver and further catalyst components on the support by impregnation. However, at a higher total pore volume, the support, or the catalyst made therefrom, may have lower crush strength.

As used herein, the pore size distribution and the pore volumes are as measured by mercury intrusion to a pressure of $3.0 \times 10^8$ Pa using a Micromeretics Autopore 9200 model (130° contact angle, mercury with a surface tension of 0.473 N/m, and correction for mercury compression applied).

The preferred alumina support comprises typically α-alumina in a quantity of at least 80% w, 90% w, or 95% w α-alumina, for example up to 99.9% w, in particular up to 99% w, relative to the weight of the catalyst. Typically, the preferred alumina support further comprises a bond material which is based on a silica-containing composition comprising a crystallization inhibitor, inhibiting the formation of crystalline silica-containing compositions. Typically, the bond material provides a coating of a silica compound to the support surface, which makes the support surface more receptive to added metal components. The bond material may typically represent from 1 to 15% w, in particular from 2 to 10% w, relative to the weight of the catalyst. Silica-containing compositions for use as a bond material are typically based on an amorphous silica compound, for example, a silica sol, a precipitated silica, an amorphous silica, or an amorphous alkali metal silicate or aluminasilicate. Typically, silica-containing compositions for use as a bond material may be based, as further components, on hydrated alumina, such as boehmite, gibbsite, bayerite or diaspore, and a crystallization inhibitor, for example, an alkali metal compound, in particular a water soluble salt, such as a sodium or potassium salt.

It has been found that the performance of the catalyst may be enhanced if the support is washed, to remove soluble residues, before deposition of other catalyst ingredients on the support. On the other hand, unwashed supports may also be used successfully. A useful method for washing the support comprises washing the support in a continuous fashion with hot, demineralised water, until the electrical conductivity of the effluent water does not further decrease. A suitable temperature of the demineralised water is in the range of 80 to 100° C., for example 90° C. or 95° C. Reference may be made to U.S. Pat. No. 6,368,998 B1, US-2002/0010094 A1 and WO-00/15333, which are incorporated herein by reference.

Generally, the highly selective silver-based epoxidation catalysts comprise, in addition to silver, a Group IA metal, and one or more selectivity enhancing dopants selected from rhenium, molybdenum and tungsten. The highly selective catalysts comprise silver suitably in a quantity of from 10 to 500 g/kg, more suitably from 50 to 250 g/kg, on the total catalyst. The Group IA metals, as well as the selectivity enhancing dopants, may each be present in a quantity of from 0.01 to 500 mmole/kg, calculated as the element (rhenium, molybdenum, tungsten or Group IA metal) on the total catalyst. Preferably, the Group IA metal is selected from lithium, potassium, rubidium and cesium. Rhenium, molybdenum or tungsten may suitably be provided as an oxyanion, for example, as a perrhenate, molybdate, tungstate, in salt or acid form.

The quantity of silver relative to the surface area of the support is at most 0.17 $g/m^2$, typically at most 0.15 $g/m^2$ in particular at most 0.12 g/m 2, more in particular at most 0.1 $g/m^2$. In the normal practice of this invention, the quantity of silver relative to the surface area of the support is frequently at least 0.01 $g/m^2$, more frequently at least 0.02 $g/m^2$.

Of special preference are the highly selective silver-based epoxidation catalysts which comprise rhenium, in addition to silver. The highly selective silver-based epoxidation catalysts are known from U.S. Pat. No. 4,761,394 and U.S. Pat. No. 4,766,105, which are incorporated herein by reference. Broadly, they comprise silver, rhenium or compound thereof, a further metal or compound thereof and optionally a rhenium co-promoter which may be selected from one or more of sulfur, phosphorus, boron, and compounds thereof, on the support material. More specifically the further metal is selected from the group of Group IA metals, Group IIA metals, molybdenum, tungsten, chromium, titanium, hafnium, zirconium, vanadium, thallium, thorium, tantalum, niobium, gallium and germanium and mixtures thereof. Preferably the further metal is selected from the Group IA metals such as lithium, potassium, rubidium and cesium and/or from the Group IIA metals such as calcium and barium. Most preferably it is lithium, potassium and/or cesium. Where possible, rhenium, the further metal or the rhenium co-promoter is typically provided as an oxyanion, in salt or acid form.

Preferred amounts of the components of these catalysts are, when calculated as the element on the total catalyst:
 silver from 10 to 500 g/kg,
 rhenium from 0.01 to 50 mmole/kg,
 the further metal or metals from 0.1 to 500 mmole/kg each, and, if present, the rhenium co-promoter or co-promoters from 0.1 to 30 mmole/kg each.

The preparation of the catalysts is known in the art and the known methods are applicable to this invention. Methods of preparing the catalyst include impregnating the support with a silver compound and with other catalyst ingredients, and performing a reduction to form metallic silver particles. Reference may be made, for example, to U.S. Pat. No. 4,761,394, U.S. Pat. No. 4,766,105, U.S. Pat. No. 5,380,697, U.S. Pat. No. 5,739,075, U.S. Pat. No. 6,368,998 B1, U.S. Pat. No. -2002/0010094 A1, WO-00/15333, WO-00/15334 and WO-00/15335, which are incorporated herein by reference.

This invention may be applied to new catalysts, as well as, for example, to catalysts during their use in an epoxidation process, or to used catalysts which, due to a plant shut-down, have been subjected to a prolonged shut-in period.

The invention may also be applied to a precursor of the catalyst. By a precursor of the catalyst is meant the supported composition which comprises the silver in unreduced, i.e. cationic form, and which further comprises the components necessary for obtaining after reduction the intended highly selective catalyst. In this case, the reduction may be effected during the contacting with the feed comprising oxygen at a temperature above 250° C.

Although the invention may be practiced in many ways, it is preferred to practice it as a gas phase process, i.e. a process in which the feed is contacted in the gas phase with the catalyst which is present as a solid material, typically in a packed bed positioned in a reactor, which may be a tubular reactor. Frequently, in commercial scale operation, the invention may be applied to a quantity of catalyst which is at least 10 kg, for example at least 20 kg, frequently in the range of from $10^2$ to $10^7$ kg, more frequently in the range of from $10^3$ to $10^6$ kg. Generally the process is carried out as a continuous process. The reactor is typically equipped with heat exchange facilities to heat or cool the catalyst. As used herein, the feed is considered to be the composition which is contacted with the catalyst. As used herein, the catalyst temperature or the temperature of the catalyst bed is deemed to be the weight average temperature of the catalyst particles.

When new catalysts are utilised, it may be useful in some instances to pretreat these catalysts prior to carrying out the invention by subjecting them to a high temperature with an inert sweeping gas passing over the catalyst. The sweeping gas is for example nitrogen or argon, or mixtures comprising nitrogen and/or argon. The high catalyst temperature converts a significant portion of organic nitrogen compounds which may have been used in the manufacture of the catalysts to nitrogen containing gases which are swept up in the gas stream and removed from the catalyst. In addition, any moisture may be removed from the catalyst. Typically, when the catalyst is loaded in a reactor, by utilizing the heater, the temperature of the catalyst is brought up to 200 to 250° C. and the gas flow is passed over the catalyst. The start-up of used catalysts may or may not require the use of a sweeping gas, but it may frequently be used. Further details on these procedures may be found in U.S. Pat. No. 4,874,879, which is incorporated herein by reference.

In accordance with this invention, the catalyst is treated by contacting it with a feed comprising oxygen at a temperature above 250° C. for a duration of up to 150 hours, which treatment may herein be referred to by the term "heat treatment". Typically any temperature above 250° C., more typically at least 255° C., may be employed, for example up to 320° C., typically up to 300° C., more typically up to 280° C. The duration of the heat treatment is typically at least 0.5 hours, preferably in the range of from 1 to 50 hours, in particular from 2 to 40 hours. The feed which may be employed in the heat treatment may be any oxygen containing feed, which may be pure oxygen or it may comprise additional components which are inert or non-inert under the prevailing conditions. Suitably, the feed is a mixture of oxygen with an inert gas, such as argon, helium, and nitrogen, or a saturated hydrocarbon. Such mixtures may be, for example, air, oxygen enriched air, or air/methane mixtures. The quantity of oxygen in the feed is preferably in the range of from 1 to 30% v, in particular from 2 to 25% v, relative to the total feed. The inert and non-inert components may be selected amongst those which may be components of the feed of an epoxidation process as described hereinafter, and the quantities in which they may be present may be in the ranges as described hereinafter. For example, the feed may comprise an olefin, in which case the olefin will at least partly be converted into the corresponding epoxide, and in which case the heat of formation of the olefin oxide may assist in accomplishing and controlling the desired temperature. Another advantage of having an olefin present in the heat treatment is that the improvement in selectivity of the catalyst may be monitored by monitoring the rate of conversion of the olefin: for example, in a continuous process a stabilization of a declining rate indicates that the selectivity improvement is near completion. It may be advantageous to apply in the heat treatment a lower oxygen concentration and a lower olefin concentration in the feed, compared with the feed composition in later stages of the process during normal olefin oxide production. Lower oxygen concentration and a lower olefin concentration in the feed will reduce the oxygen conversion level so that, advantageously, hot spots in the catalyst are better avoided and the process will be more easily controllable.

Thus, in the heat treatment the feed may comprise, in addition to oxygen, an olefin, carbon dioxide, inert gas, saturated hydrocarbon, and/or reaction modifiers, such as an organic halide or a nitrate- or nitrite-forming compound. However, in the heat treatment, the presence of one or more of these additional components in the feed is not considered to be essential to the invention.

The heat treatment may typically be carried at an absolute pressure in the range of from 1000 to 4000 kPa. Preferably, when this step is carried out as a gas phase process involving a packed catalyst bed, the GHSV is in the range of from 1500 to 10000 Nl/(l.h). "GHSV" or Gas Hourly Space Velocity is the unit volume of gas at normal temperature and pressure (0° C., 1 atm, i.e. 101.3 kPa) passing over one unit volume of packed catalyst per hour.

Following the heat treatment, the catalyst temperature is decreased to a temperature of at most 250° C., in particular to a temperature of at most 245° C.

If the present heat treatment is conducted as a separate process, e.g. not incorporated as a step in an epoxidation process, subsequent to the heat treatment the catalyst temperature may be decreased to a temperature which is suitable for storage of the catalyst, for example a temperature in the range of from 0 and 50° C., in particular from 10 to 40° C. After storage, the catalyst may be applied in an epoxidation process.

It is advantageous to incorporate the heat treatment as a step in an epoxidation process, in which case in the heat treatment the feed may comprise at least oxygen and the olefin, and the corresponding olefin oxide is formed as a reaction product. The heat treatment may be incorporated in the epoxidation process in any phase of the epoxidation process, for example during the start up or during the regular olefin oxide production. In such case, the heat treatment represents an increase in catalyst temperature from the prevailing catalyst operating temperature, followed by a decrease in temperature to a level which is desirable as an operating temperature of the catalyst.

The following description may relate to an epoxidation process which incorporates, as one of its steps, the present heat treatment. It may also relate to an epoxidation process which employs a catalyst which has previously been subjected to the heat treatment. The epoxidation process may be carried out by using methods known in the art. Reference may be made, for example, to U.S. Pat. No. 4,761,394, U.S. Pat. No. 4,766,105, U.S. Pat. No. 6,372,925 B1, U.S. Pat. No. 4,874,879 and U.S. Pat. No. 5,155,242, which are incorporated herein by reference.

The olefin for use in the epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene.

The epoxidation process may be air-based or oxygen-based, see Kirk-Othmer's *Encyclopedia of Chemical Technology*, 3rd ed., Vol. 9, 1980, p. 445-447. In the air-based process air or air enriched with oxygen is employed as the source of the oxidizing agent while in the oxygen-based processes high-purity (>95 mole-%) oxygen is employed as the source of the oxidizing agent. Presently most epoxidation plants are oxygen-based and this is a preferred embodiment of the present invention.

Oxygen is typically applied at a concentration which avoids the flammable regime. The concentration of oxygen in the feed may be adjusted as the concentration of the olefin is changed so as to remain outside the flammable regime. The actual safe operating ranges depend, along with the feed composition, also on the epoxidation conditions such as the catalyst temperature and the pressure.

A reaction modifier may be present in the feed for increasing the selectively, suppressing the undesirable oxidation of ethylene or ethylene oxide to carbon dioxide and water, relative to the desired formation of ethylene oxide. Many organic compounds, especially organic halides, may be employed as the reaction modifier (cf. for example EP-A-352850, U.S. Pat. No. 4,761,394 and U.S. Pat. No. 4,766,105, which are incorporated herein by reference). Organic nitrogen compounds or inorganic nitrogen compounds such as nitrogen oxides, hydrazine, hydroxylamine or ammonia may be employed as well, but this is generally less preferred. It is considered that under the operating conditions of the epoxidation process the nitrogen containing reaction modifiers are precursors of nitrates or nitrites, i.e. they are so-called nitrate- or nitrite-forming compounds (cf. for example EP-A-3642 and U.S. Pat. No. 4,822,900, which are incorporated herein by reference).

The organic halide is in particular an organic bromide, and more in particular an organic chloride. Preferred organic halides are chlorohydrocarbons or bromo-hydrocarbons. More preferably they are selected from the group of methyl chloride, ethyl chloride, ethylene dichloride, ethylene dibromide, vinyl chloride or a mixture thereof. Most preferred reaction modifiers are ethyl chloride and ethylene dichloride.

Although the organic halide may be supplied as a single compound, upon contact with the catalyst a variety of compounds may be formed which function as reaction modifier, and which may be present in the feed if a recycle is applied. For example, when applying ethyl chloride in an ethylene oxide process, the feed may in practice comprise ethyl chloride, vinyl chloride, ethylene dichloride and methyl chloride.

In embodiments, amongst others, nitrate- or nitrite-forming compounds, e.g. nitrogen oxides and/or organic nitrogen compounds, are used as reaction modifier together with the organic halide, in particular an organic chloride. Suitable nitrogen oxides are of the general formula $NO_x$ wherein x, which denotes the ratio of the number of oxygen atoms to the number of nitrogen atoms, is in the range of from 1 to 2. These nitrogen oxides include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. Hydrazine, hydroxylamine or ammonia may be employed as well.

The feed may comprise one or more optional components, such as carbon dioxide, inert gases and saturated hydrocarbons. Carbon dioxide is a by-product in the epoxidation process. However, carbon dioxide generally has an adverse effect on the catalyst activity, and high concentrations of carbon dioxide are therefore typically avoided. The inert gas may be, for example, nitrogen or argon, or a mixture thereof. Suitable saturated hydrocarbons are propane and cyclopropane, and in particular methane and ethane. Saturated hydrocarbons may be added to the feed in order to increase the oxygen flammability limit.

Typically, in the initial phase of the epoxidation process, the catalyst temperature may be in the range of from 180 to 250° C., more typically in the range of from 200 to 245° C. Such temperatures are in particular suitable as long as the catalyst has not yet substantially been subject to an aging-related performance decline. Such aging manifests itself by a reduction in the activity of the catalyst. When a reduction in activity of the catalyst is manifest, the catalyst temperature may be increased in order to compensate for the reduction in activity. The catalyst temperature may ultimately be increased to values above 250° C., for example up to a temperature of 325° C., typically in the range of from 270 to 300° C. Generally speaking, the catalyst temperature may be increased until it becomes undesirably high, at which point in time the catalyst is deemed to be at the end of its lifetime and would need to be exchanged. Typically, the olefin concentration in the feed is at most 80 mole-%, relative to the total feed. Preferably, it is in the range of from 0.5 to 70 mole-%, in particular from 1 to 60 mole-%, on the same basis. If desired, the olefin concentration may be increased during the lifetime of the catalyst, by which the selectivity may be improved in an operating phase wherein the catalyst has aged (cf. U.S. Pat. No. 6,372,925 B1, which is incorporated herein by reference).

Typically, the concentration of oxygen is within the range of from 1 to 15 mole-%, more typically from 2 to 10 mole-% of the total feed.

Typically, concentrations of carbon dioxide in the feed in excess of 10 mole-%, preferably in excess of 5 mole-%, relative to the total feed, are avoided. A concentration of carbon dioxide as low as 1 mole-% or lower, relative to the total feed, may be employed. Inert gas may be present in the feed in a concentration of from 0.5 to 95 mole-%. In an air based process inert gas may be present in the feed in a concentration of from 30 to 90 mole-%, typically from 40 to 80 mole-%. In an oxygen based process inert gas may be present in the feed in a concentration of from 0.5 to 30 mole-%, typically from 1 to 15 mole-%. If saturated hydrocarbons are present, they may be present in a quantity of up to 80 mole-%, relative to the total feed, in particular up to 75 mole-%. Frequently they are present in a quantity of at least 30 mole-%, more frequently at least 40 mole-%.

The reaction modifiers are generally effective when used in low quantities in the feed, for example up to 0.1 mole-%, relative to the total feed, for example from $0.01 \times 10^{-4}$ to 0.01 mole-%. In particular when the olefin is ethylene, it is preferred that the reaction modifier is present in the feed at a quantity of from $0.05 \times 10^{-4}$ to $50 \times 10^{-4}$ mole-%, in particular from $0.2 \times 10^{-4}$ to $30 \times 10^{-4}$ mole-%, relative to the total feed.

Suitable quantities of the reaction modifiers in the feed may also be expressed in relation to the quantity of hydrocarbons present in the feed. The relative quantity Q of the reaction modifier is the ratio of the effective molar quantity of active species of the reaction modifier present in the feed to the effective molar quantity of hydrocarbons present in the feed, both molar quantities being expressed in the same units, for example as mole-%, based on the total feed.

When the reaction modifier is a halogen compound, for the purpose of calculating the effective molar quantity of active species of the reaction modifier and the value of Q, the number of active species is deemed to be the number of halogen atoms present, and when the reaction modifier is a nitrate- of nitrite-forming compound, the number of active species is deemed to be the number of nitrogen atoms present. This implies, for example, that 1 mole of ethylene dichloride provides 2 moles of active species, i.e. all of the chlorine atoms present provide an active species. On the other hand, reaction modifiers which are methyl compounds, such as methyl chloride and methyl bromide, are less responsive and therefore from 2 to 5 moles, in particular from 2.5 to 3.5 moles, suitably 3 moles of the methyl compounds may be deemed to provide 1 mole of the active species. This number may be determined and verified by routine experimentation, and—without wishing to be bound by theory—it is believed that this number is higher as the methyl compound in question has a lesser ability to split off the heteroatom in question (for example the halogen or nitrogen atom). Thus, for example, when the feed comprises $2 \times 10^{-4}$ mole-% of ethyl chloride, $3 \times 10^{-4}$ mole-% of vinyl chloride, $1 \times 10^{-4}$ mole-% of ethylene dichloride and $1.5 \times 10^{-4}$ mole-% of methyl chloride, the effective molar quantity of active species of the reaction modifier may be calculated to amount to $(2 \times 10^{-4} \times 1) + (3 \times 10^{-4} \times 1) + (1 \times 10^{-4} \times 2) + (1.5 \times 10^{-4} \times 1/3) = 7.5 \times 10^{-4}$ mole-%.

In other words, the effective molar quantity of active species of the reaction modifier present in the feed may be calculated by multiplying the molar quantity of each of the reaction modifiers present in the feed with a factor, and adding up the multiplication products, wherein each factor represents the number of active heteroatoms, in particular halogen atoms and/or nitrogen atoms, present per molecule of the reaction modifier in question, on the understanding that the factor for a reaction modifier which is a methyl compound may be in the range of from 1/5 to 1/2, more typically from 1/3.5 to 1/2.5, suitably 1/3.

The hydrocarbons present in the feed comprise the olefin and any saturated hydrocarbon present. The hydrocarbons present in the feed are deemed to have the ability to remove/strip reaction modifier from the catalyst surface and the extent to which they have this ability may differ for the various hydrocarbons. In order to account for these differences (relative to ethylene), the molar quantity of each of the hydrocarbons present is multiplied with a factor, before the molar quantities are added up to calculate the effective molar quantity of the hydrocarbons. Herein, the factor of ethylene is 1, by definition; the factor for methane may be in the range of from 0.1 to 0.5, or lower, for example down to 0, more typically from 0.2 to 0.4; the factor for ethane may be in the range of from 50 to 150, more typically from 70 to 120; and the factor for higher hydrocarbons (i.e. having at least 3 carbon atoms) may be in the range of from 10 to 10000, more typically from 50 to 2000. Such factors may be determined and verified by routine experimentation, and—without wishing to be bound by theory—it is believed that the factor is higher as the hydrocarbon in question has a greater ability to form radicals. Suitable factors for methane, ethane, propane and cyclopropane, relative to ethylene, are 0.3, 85, 1000 and 60, respectively. As an example, when the feed comprises 30 mole-% ethylene, 40 mole-% of methane, 0.4 mole-% of ethane and 0.0001 mole-% of propane, the effective molar quantity of the hydrocarbons may be calculated to amount to $(30 \times 1) + (40 \times 0.3) + (0.4 \times 85) + (0.0001 \times 1000) = 76.1$ mole-%.

It is noted that when ethylene oxide is produced from ethylene without further hydrocarbons being present, the effective molar quantity of the hydrocarbons equals the actual molar quantity, and that the addition of ethane or higher hydrocarbons to an ethylene feed contributes significantly to the effective molar quantity, whereas there is relatively little contribution from any methane added. In some embodiments, the factor for methane may be taken as 0, thus neglecting, for example for reasons of convenience, the influence of methane.

Eligible values of Q are at least $1 \times 10^{-6}$, and in particular at least $2 \times 10^{-6}$. Eligible values of Q are at most $100 \times 10^{-6}$, and in particular at most $50 \times 10^{-6}$.

At any moment of the epoxidation process, the value of Q may be adjusted so as to achieve an optimal selectivity towards the olefin oxide formation. In practice, the value of Q may be adjusted by adjusting the quantity of the reaction modifier present in the feed, while not changing the hydrocarbon concentrations in the feed.

As indicated hereinbefore, during the epoxidation process the catalyst temperature may be increased, for example, in order to compensate for a reduction in activity which is related to catalyst ageing. Deviations from the optimum selectivity which would result from a change in temperature may be reduced or even prevented, by adjusting the value of Q proportionally with the change in catalyst temperature. So, when the catalyst temperature is changed from $T_1$ to $T_2$, the value of Q may be changed from $Q_1$ to substantially $Q_2$, according to the formula $$Q_2 = Q_1 + B(T_2 - T_1),$$

wherein B denotes a constant factor, in $(° C.)^{-1}$, which is greater than 0. Suitable values of B may be determined and verified by routine experimentation. The value of B is typically in the range of from $0.01 \times 10^{-6}$, to $1 \times 10^{-6}$, in particular from $0.1 \times 10^{-6}$ to $0.5 \times 10^{-6}$. A suitable value of B amounts to $0.22 \times 10^{-6}$, in particular when used in combination with the numbers and factors employed in the example calculations of the effective molar quantity of active species of the reaction modifier and the effective molar quantity of the hydrocarbons, as given hereinbefore.

It is preferred to operate at the catalyst temperature $T_1$ employing such a value of $Q_1$ that the selectivity towards the olefin oxide formation is optimal. When this is the case, the epoxidation process will continue to operate at an optimum selectivity, but not necessarily the same selectivity, when employing the catalyst temperature $T_2$ and substantially the value of $Q_2$ as calculated in accordance with formula (I).

Further reaction conditions of the epoxidation process may be selected from wide ranges, as set out hereinafter. The reactor inlet pressure is typically in the range of from 1000 to 4000 kPa absolute. Preferably, when the epoxidation process is carried out as a gas phase process involving a packed catalyst bed, the GHSV is in the range of from 1500 to 10000

Nl/(l.h). Preferably, the work rate is in the range of from 0.5 to 10 kmole olefin oxide produced per m$^3$ of catalyst per hour, in particular 0.7 to 8 kmole olefin oxide produced per m$^3$ of catalyst per hour, for example 5 kmole olefin oxide produced per m$^3$ of catalyst per hour. As used herein, the work rate is the amount of the olefin oxide produced per unit volume of catalyst per hour and the selectivity is the molar quantity of the olefin oxide formed relative to the molar quantity of the olefin converted.

The olefin oxide produced may be recovered from the reactor product by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol or a 1,2-diol ether.

The olefin oxide produced in the present epoxidation process may be converted into a 1,2-diol, a 1,2-diol ether, or an alkanolamine. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The conversion into the alkanolamine may comprise, for example, reacting the olefin oxide with ammonia. Anhydrous or aqueous ammonia may be used, although anhydrous ammonia is typically used to favour the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the organic compounds mentioned herein, for example the olefins, 1,2-diols, 1,2-diol ethers and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

The following examples will illustrate the invention, without limiting the scope of the invention.

EXAMPLES 1-4

Example 1 for Comparison, Examples 2-4 According to the Invention

Preparation of a Support

A support was made by mixing the following ingredients:
1. 67.4 parts by weight (pbw) of an α-alumina with $d_{50}$ of 29 μm;
2. 29 pbw of an α-alumina with $d_{50}$ of 3 μm;
3. 3 pbw of aluminium oxide (in the form of boehmite);
4. 0.5 pbw of silica (in the form of ammonia stabilized silica sol); and
5. 0.1 pbw of sodium oxide (in the form of sodium acetate).

The average particle size, referred to herein as "$d_{50}$", is as measured by a Horiba LA900 particle size analyzer and represents a particle diameter at which there are equal spherical equivalent volumes of particles larger and particles smaller than the stated average particle size. The method includes dispersing the particles by ultrasonic treatment, thus breaking up secondary particles into primary particles. This sonification treatment is continued until no further change in the $d_{50}$ value is noticed, which typically requires 5 minute sonification when using the Horiba LA900 particle size analyzer.

To this mixture were added 5% w, relative to the mixture weight, of petroleum jelly and 9% w, relative to the mixture weight, of burnout material and 0.1% w, relative to the mixture weight, of boric acid. Water (about 30% w, relative to the mixture weight) was then added in an amount to make the mixture extrudable and this mixture was then extruded to form formed bodies in the form of hollow cylinders that are about 8 mm in diameter and 8 mm long. These were then dried and fired in a kiln at 1425° C., for 4 hours in air to produce Support A. As regards procedures followed in this support preparation, reference may be made to U.S. Pat. No. 5,100,859.

The surface area of the support so prepared was 2.0 m$^2$/g. The total pore volume was 0.41 ml/g and the volume of the pores having diameters in the range 0.2-10 μm was 0.37 ml/g, relative to the weight of the support. The pore size distribution was as follows: the pores having diameters in the range <0.2 μm represent 5% v, the pores having diameters in the range 0.2-10 μm represent 92% v, and the pores having diameters in the range >10 μm represent 3% v, relative to the total pore volume.

The support was subjected to washing with boiling de-ionised water following the method as disclosed in US-2002/0010094 A1, paragraph 0034. The dried support was then used for the preparation of a catalyst.

Catalyst Preparation

A silver-amine-oxalate stock solution was prepared by the following procedure:

415 g of reagent-grade sodium hydroxide were dissolved in 2340 ml de-ionized water and the temperature was adjusted to 50° C.

1699 g high purity "Spectropure" silver nitrate was dissolved in 2100 ml de-ionized water and the temperature was adjusted to 50° C.

The sodium hydroxide solution was added slowly to the silver nitrate solution, with stirring, while maintaining a solution temperature of 50° C. This mixture was stirred for 15 minutes, then the temperature was lowered to 40° C.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 μmho/cm. 1500 ml fresh deionized water was then added.

630 g of high-purity oxalic acid dihydrate were added in approximately 100 g increments. The temperature was keep at 40° C. and the pH was kept above 7.8.

Water was removed from this mixture to leave a highly concentrated silver-containing slurry. The silver oxalate slurry was cooled to 30° C.

699 g of 92% w ethylenediamine (8% w de-ionized water) was added while maintaining a temperature no greater than 30° C. The resulting silver-amine-oxalate stock solution contained approximately 27-33% w silver.

Impregnation solutions were prepared by adding aqueous solutions comprising predetermined quantities of lithium hydroxide, ammonium perrhenate, ammonium metatungstate, cesium hydroxide (optional), and water to samples of a silver-amine-oxalate stock solution as described. The quantities were predetermined by calculation based on the desired composition of the catalyst to be prepared.

A sample of the support, prepared as indicated under the heading "Preparation of Supports", was impregnated with the impregnation solution and dried, as follows. The support sample was placed under a 25 mm Hg vacuum for 1 minute at ambient temperature. The impregnation solution, approximately 1.6 g/g support, was then introduced to submerse the support, and the vacuum was maintained at 25 mm Hg for an additional 3 minutes. The vacuum was then released and the excess impregnation solution was removed from the catalyst pre-cursor by centrifugation at 500 rpm for two minutes. The catalyst pre-cursor was then dried while being shaken at 250° C. for 5.5 minutes in a stream of air. The catalyst so prepared contained 14.5% w silver, 2.0 mmole/kg rhenium, 2.0 mmole/kg tungsten, 7.2 mmole/kg cesium and 40 mmole/kg lithium, all relative to the weight of the catalyst.

Catalyst Testing

The catalyst so prepared was tested in the production of ethylene oxide from ethylene and oxygen. To do this, 1.5 to 2.0 g samples of crushed catalyst were loaded into four stainless steel U-shaped tubes. The tubes were immersed in a molten metal bath (heat medium) at 180° C., and the ends of each tube were connected to a gas flow system. A gas mixture passed through the catalyst beds, in a "once-through" operation. The weight of catalyst used and the inlet gas flow rate were adjusted to give a gas hourly space velocity of 6800 Nl/(l.h). The inlet gas pressure was 1550 kPa absolute. The composition of the gas mixture was adjusted to 25% v ethylene, 7% v oxygen, 5% v carbon dioxide, 2.5 ppmv ethyl chloride, and nitrogen balance.

The temperature of each of the catalyst beds was ramped up at a rate of 10° C. per hour to 225° C. and then the temperature was adjusted so as to achieve an ethylene oxide content of 1.5% v in each of the outlet gas streams. For each catalyst bed, the ethyl chloride concentration in the gas mixture was adjusted to 2.5 ppmv so as to obtain an optimum selectivity at a constant ethylene oxide concentration in the outlet gas stream. These conditions were maintained for 100 hours, at which time the catalyst has equilibrated in performance. Table I provides the performance of each of the catalysts, in terms of the temperature and the selectivity, as measured after lapse of this period of 100 hours. A higher temperature needed to accomplish a certain ethylene oxide content in the outlet gas stream indicates a lower activity of the catalyst.

Then through each of the catalyst beds a different gas mixture was passed, as indicated in Table I, and the temperature of each of the catalyst beds was increased to 260° C. for a period of 24 hours. After this period, the conditions were returned to those employed immediately before the temperature increase, and the temperature of each of the catalyst beds was adjusted so as to restore the ethylene oxide content of 1.5% v in each of the outlet gas streams. For each catalyst bed, the ethyl chloride concentration in the gas mixtures was readjusted to 1.5 ppmv.

Table I provides for each of the catalysts the catalyst temperature and the selectivity, immediately after re-adjusting the ethyl chloride concentration.

TABLE I

| Example | Gas composition during heat treatment at 260° C. | Prior to 24 hours at 260° C. | | After 24 hours at 260° C. | |
|---|---|---|---|---|---|
| | | Temperature (° C.) | Selectivity (% - mole) | Temperature (° C.) | Selectivity (% - mole) |
| 1 *) | Nitrogen only | 222 | 82.0 | 223 | 84.4 |
| 2 **) | 9.4% v oxygen, 6.7% v carbon dioxide, balance: nitrogen | 224 | 82.0 | 242 | 88.6 |
| 3 **) | 9.4% v oxygen, 6.7% v carbon dioxide, 0.5 ppmv ethyl chloride, balance: nitrogen | 222 | 82.1 | 242 | 89.3 |
| 4 **) | 5.0% v ethylene, 7.0% v oxygen, 5.0% v carbon dioxide, ethyl chloride ***), balance: nitrogen | 224 | 83.0 | 240 | 89.4 |

*) for comparison
**) according to the invention
***) trace, <0.1 ppmv

Further catalysts were prepared and tested in a similar manner, giving similar results. Such catalysts comprised, for example, 14.5% w silver, 2.0 mmole/kg rhenium, 6.0 mmole/kg cesium and 40 mmole/kg lithium; or 14.5% w silver, 2.0 mmole/kg rhenium, 1.0 mmole/kg tungsten, 7.2 mmole/kg cesium and 40 mmole/kg lithium, all relative to the weight of the catalysts.

EXAMPLE 5-8

Example 5 for Comparison, Examples 6-8 According to the Invention

Samples (1.5 to 2.0 g) of the crushed catalyst of Examples 1-4 were loaded into four stainless steel U-shaped tubes. The tubes were immersed in a molten metal bath (heat medium) at 180° C., and the ends of each tube were connected to a gas flow system. A gas mixture passed through the catalyst beds, in a "once-through" operation. The weight of catalyst used and the inlet gas flow rate were adjusted to give a gas hourly space velocity of 6800 Nl/(l.h). The inlet gas pressure was 1550 kPa absolute.

In Examples 6, 7 and 8, the catalyst was first pretreated at 260° C. for 4, 12 and 24 hours, respectively, with a gas mixture of 17.5% v oxygen and 82.5% v nitrogen. Then the temperature was decreased to 225° C., and the gas mixture was adjusted to 25% v ethylene, 7% v oxygen, 5% v carbon dioxide, 1.5 ppmv ethyl chloride, and nitrogen balance. In Example 5, the pretreatment was omitted.

The temperature of each of the catalyst beds was ramped up at a rate of 10° C. per hour to 245° C. and then the temperature was adjusted so as to achieve an ethylene oxide content of 1.5% v in each of the outlet gas streams. For each catalyst bed, the ethyl chloride concentration in the gas mixture was adjusted to 1.5 ppmv so as to obtain an optimum selectivity at a constant ethylene oxide concentration (1.5% v) in the outlet gas stream. These conditions were maintained for 100 hours production time, at which time the catalyst has equilibrated in performance.

Table II provides for each of the catalysts the final temperature and selectivity.

TABLE II

| Example | Duration (h) at 260° C. | Catalyst temperature (° C.) | Selectivity (%-mole) |
|---|---|---|---|
| 5 *) | 0 | 226 | 83.5 |
| 6 **) | 4 | 237 | 88.8 |
| 7 **) | 12 | 245 | 89.4 |
| 8 **) | 24 | 252 | 89.8 |

*) for comparison
**) according to the invention

Further catalysts were prepared and tested in a similar manner, giving similar results. Such catalysts comprised, for example, 14.5% w silver, 3.0 mmole/kg rhenium, 3.0 mmole/kg tungsten, 7.5 mmole/kg cesium and 20 mmole/kg lithium, all relative to the weight of the catalyst.

EXAMPLE 9-12

Example 9 for Comparison, Examples 10-12 According to the Invention

Samples (1.5 to 2.0 g) of the crushed catalyst of Examples 1-4 were loaded into four stainless steel U-shaped tubes. The tubes were immersed in a molten metal bath (heat medium) at 180° C., and the ends of each tube were connected to a gas flow system. A gas mixture passed through the catalyst beds, in a "once-through" operation. The weight of catalyst used and the inlet gas flow rate were adjusted to give a gas hourly space velocity of 6800 Nl/(l.h). The inlet gas pressure was 1550 kPa absolute.

The composition of the gas mixture was adjusted to 25% v ethylene, 7% v oxygen, 5% v carbon dioxide, 2.5 ppmv ethyl chloride, and nitrogen balance.

The temperature of each of the catalyst beds was ramped up at a rate of 10° C. per hour to 225° C. and then the temperature was adjusted so as to achieve an ethylene oxide content of 1.5% v in each of the outlet gas streams. For each catalyst bed, the ethyl chloride concentration in the gas mixture was adjusted to 2.5 ppmv so as to obtain an optimum selectivity at a constant ethylene oxide concentration in the outlet gas stream. These conditions were maintained for 100 hours, at which time the catalyst has equilibrated in performance.

In Examples 10, 11 and 12, the temperature of the catalyst beds was then increased to 260° C. for a period of 4, 12 and 24 hours, respectively, during which period through the catalyst bed a gas mixture of 9.5% v oxygen, 6.8% v carbon dioxide and nitrogen (balance) was passed. After this period, the temperature was decreased to 225° C. and the gas mixture was adjusted to 25% v ethylene, 7% v oxygen, 5% v carbon dioxide, 1.5 ppmv ethyl chloride, and nitrogen balance. In Example 9, the temperature and the composition of the gas mixture were not changed.

Table III provides for each of the catalysts the final temperature and selectivity.

TABLE III

| Example | Duration (h) at 260° C. | Catalyst temperature (° C.) | Selectivity (%-mole) |
|---|---|---|---|
| 9 *) | 0 | 230 | 83.0 |
| 10 **) | 4 | 237 | 88.0 |
| 11 **) | 12 | 247 | 89.5 |
| 12 **) | 24 | 242 | 89.5 |

*) for comparison
**) according to the invention

Examples 2-4, 6-8 and 10-12 (according to the invention), compared with Examples 1, 5 and 9 (comparative), show that after exposing the catalyst to an oxygen containing gas at a high temperature, for example 260° C., the catalyst exhibits an improved selectivity when it is subsequently used during normal operation in an epoxidation process. It is striking that higher selectivities were found, although the catalysts were operated at a higher temperature to achieve the same ethylene content in the reactor outlet gas streams. The invented method for increasing the selectivity of the catalyst may be incorporated as a step in an epoxidation process, such as in Examples 2-4 and 10-12, or the method be carried out prior to the epoxidation process, such as in Examples 6-8.

What is claimed:

1. A method for improving the selectivity of a supported highly selective epoxidation catalyst comprising silver in a quantity of at most 0.17 g per m$^2$ surface area of the support and further comprising rhenium or compound thereof, which method comprises
   contacting the catalyst, or a precursor of the catalyst comprising the silver in cationic form, with a feed comprising oxygen at a catalyst temperature above 250° C. for a duration of at least 1 hour and up to 150 hours, and
   subsequently decreasing the catalyst temperature to a value of at most 250 ° C.

2. A method as claimed in claim 1, wherein the catalyst, or the precursor of the catalyst, comprises an α-alumina support having a surface area of at least 1 m$^2$/g, and a pore size distribution such that pores with diameters in the range of from 0.2 to 10 μm represent at least 70 % of the total pore volume and such pores together provide a pore volume of at least 0.25 ml/g, relative to the weight of the support.

3. A method as claimed in claim 1, wherein the catalyst, or the precursor of the catalyst, comprises, in addition to silver, a Group IA metal.

4. A method as claimed in claim 1, wherein the catalyst, or the precursor of the catalyst, further comprises or compound thereof, selected from the group of Group IA metals, Group IIA metals, molybdenum, tungsten, chromium, titanium, hafnium, zirconium, vanadium, thallium, thorium, tantalum, niobium, gallium and germanium and mixtures thereof, and optionally a rhenium co-promoter which may be selected from one or more of sulfur, phosphorus, boron, and compounds thereof, on the support material.

5. A method as claimed in claim 1, wherein the catalyst, or the precursor of the catalyst, comprises silver in a quantity of from 50 to 250 g/kg, on the total catalyst,and the support has a surface area of from 1 to 5 m$^2$/g.

6. A method as claimed in claim 1, wherein the feed comprises oxygen in a quantity of from 1 to 30% v, relative to the total feed.

7. A method as claimed in claim 6, wherein the feed comprises oxygen in a quantity of from 2 to 25% v, relative to the total feed.

8. A method as claimed in claim 1, wherein the catalyst, or the precursor of the catalyst, is contacted with a feed comprising oxygen at a temperature in the range of from 250 to 320° C.

9. A method as claimed in claim 8, wherein the temperature in the range of from 255 to 300° C.

10. A method as claimed in claim 1, wherein the duration is in the range of from 1 to 50 hours.

11. A method as claimed in claim1, wherein the duration is in the range of from 2 to 40 hours.

12. A method as claimed in claim 1, wherein the feed comprises an olefin, in addition to oxygen.

13. A method as claimed in claim 12, wherein the feed comprises the olefin in a concentration of from 0.5 to 70 mole-%; oxygen in a concentration of from 1 to 15 mole-%; and, in addition, a saturated hydrocarbon, if any, in a concentration of from 0 to 80 mole-%, relative to the total feed.

14. A method as claimed in claim 13, wherein the feed comprises the olefin in a concentration of from 1 to 60 mole-%; oxygen in a concentration of from 2 to 10 mole-%; and a saturated hydrocarbon in a concentration of from 30 to 75 mole-%, relative to the total feed.

15. A method as claimed in claim 1, wherein the quantity of silver relative to the surface area of the support is in the range of from 0.01 to 0.15 g/m$^2$.

16. A method as claimed in claim 15, wherein the quantity of silver relative to the surface area of the support is in the range of from 0.02 to 0.12 g/m$^2$.

17. A method as claimed in claim 15, wherein the catalyst, or the precursor of the catalyst, comprises silver in a quantity of from 50 to 250 g/kg, on the total catalyst, and the catalyst comprises an α-alumina support having a surface area of from 1 to 5 m$^2$/g, and a pore size distribution such that pores with diameters in the range of from 0.2 to 10 μm represent at least 70% of the total pore volume and such pores together provide a pore volume of at least 0.25 ml/g, relative to the weight of the support.

18. A method as claimed in claim 15, wherein the catalyst, or the prcursor of the catalyst, comprises, in addition to silver, a Group IA metal.

19. A method as claimed in claim 18, wherein the catalyst, or the precursor of the catalyst, further comprises, a further metal or compound thereof selected from the group of Group IA metals, Group IIA metals, molybdenum, tungsten, chromium, titanium, hafnium, zirconium, vanadium, thallium, thorium, tantalum, niobium, gallium and germanium and mixtures thereof, and optionally a rhenium co-promoter which may be selected from one or more of sulfur, phosphorus boron, and compounds thereof, on the support material.

20. A method as claimed in claim 15, wherein the catalyst, or the precursor of the catalyst, is contacted with a feed comprising oxygen at a temperature in the range of from 250 to 320° C.

21. A method as claimed in claim 20, wherein the catalyst, or the precursor of the catalyst, is contacted with a feed comprising oxygen at a temperature in the range of from 255 to 300° C.

22. A method as claimed in claim 15, wherein the duration is in the range of from 1 to 50 hours.

23. A method as claimed in claim 22, wherein the duration is in the range of from 2 to 40 hours.

24. A method as claimed in claim 23, wherein the feed comprises the olefin in a concentration of from 0.5 to 70 mole-%; oxygen in a concentration of from 1 to 15 mole-%; and, in addition, a saturated hydrocarbon, if any, in a concentration of from 0 to 80 mole-%, relative to the total feed.

* * * * *